United States Patent [19]
Babasade

[11] Patent Number: 5,230,837
[45] Date of Patent: Jul. 27, 1993

[54] FRAGRANCE DISPENSER AND METHOD FOR FRAGRANCE DISPENSING

[76] Inventor: Wolfgang W. Babasade, 405 Knierim Pl., New Milford, N.J. 07646

[21] Appl. No.: 876,325

[22] Filed: Apr. 30, 1992

Related U.S. Application Data

[66] Substitute of Ser. No. 663,113, Mar. 1, 1991, abandoned.

[51] Int. Cl.[5] .............................................. B01F 3/04
[52] U.S. Cl. .................................. 261/30; 261/84; 261/DIG. 65; 239/44; 239/55
[58] Field of Search ............... 239/44, 47, 55; 261/84, 261/83, 30, DIG. 65; 136/246

[56] References Cited

U.S. PATENT DOCUMENTS

| | | | |
|---|---|---|---|
| 302,163 | 7/1884 | Saladin | 261/30 |
| 636,031 | 10/1899 | Ette | 261/83 |
| 712,177 | 10/1902 | Bradshaw | 261/30 |
| 725,086 | 4/1903 | Jacobs | 261/30 |
| 902,623 | 11/1908 | Subert | 239/44 |
| 1,066,851 | 7/1913 | Siefert | 261/30 |
| 1,498,355 | 6/1924 | Cox | 261/30 |
| 2,173,645 | 9/1939 | Bordner | 261/30 |
| 2,210,354 | 8/1940 | Bates | 261/30 |
| 2,397,230 | 3/1946 | Armathes | 261/84 |
| 2,556,608 | 6/1951 | Will | 239/47 |
| 2,741,003 | 4/1956 | David | 261/DIG. 65 |
| 4,327,056 | 4/1982 | Gaiser | 239/55 |
| 4,332,973 | 6/1982 | Sater | 136/246 |
| 4,568,521 | 2/1986 | Spector | 422/124 |
| 4,638,110 | 1/1987 | Erbert | 136/246 |
| 4,857,240 | 8/1989 | Kearnes et al. | 261/26 |
| 4,944,898 | 7/1990 | Glasor | 261/84 |
| 5,034,222 | 7/1991 | Kellett et al. | 239/55 |
| 5,077,102 | 12/1991 | Chong | 239/44 |

FOREIGN PATENT DOCUMENTS 831033 2/1952 Fed. Rep. of Germany ........ 239/44

Primary Examiner—Tim Miles

[57] ABSTRACT

A fragrance dispenser utilizing a fragrance dispensing wheel is described. The fragrance wheel is directly mounted onto a rotatable motor shaft, the motor being powered by either conventional A.C. or D.C. current, or by a photovoltaic cell. Absorbent panels on the wheel direct ambient air in response to motor rotation. When powered by photovoltaic cell fragrance is dispensed in an economic and safe manner in proportion to room lighting.

10 Claims, 3 Drawing Sheets

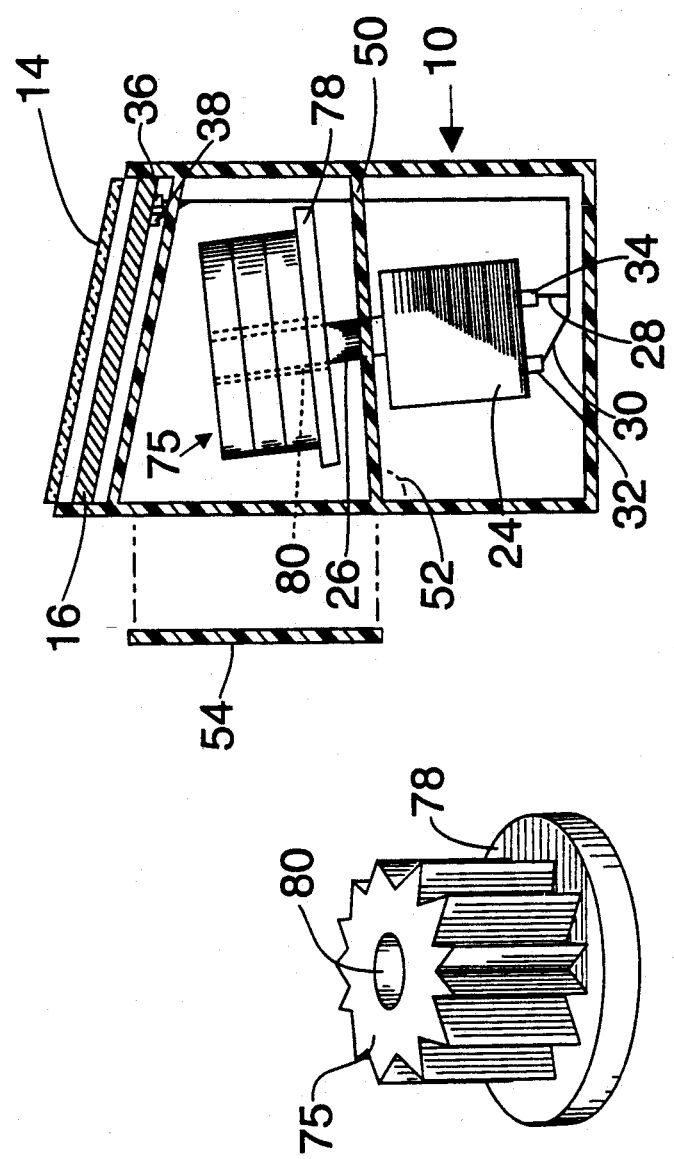
FIG. 7
FIG. 6
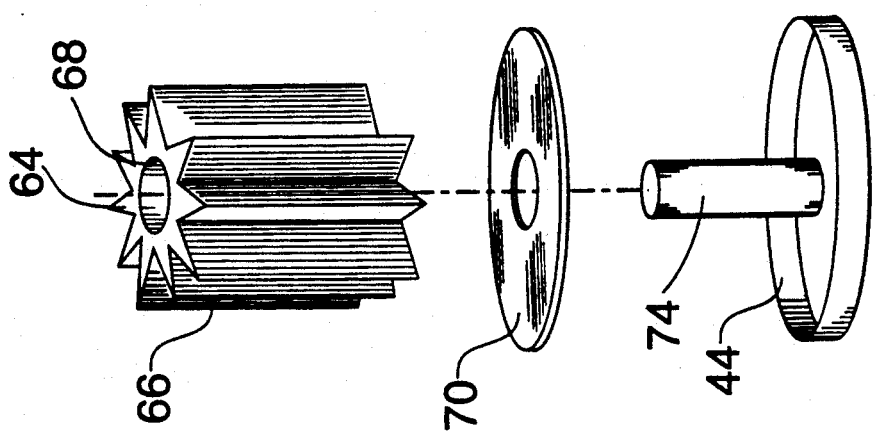
FIG. 5

FRAGRANCE DISPENSER AND METHOD FOR FRAGRANCE DISPENSING

BACKGROUND OF THE INVENTION

This application is a substitute application for my earlier U.S. application, Ser. No. 663,113, filed Mar. 1, 1991, now abandoned.

This invention relates to a fragrance dispenser and method for fragrance dispensing, and in particular wherein fragrance is dispensed by means of a fragrance dispensing wheel.

It is often desirable and necessary to change the characteristics of ambient air in an enclosed environment, as, for example, a room. This can be accomplished by employing an aromatic substance dispenser in the room to mask an offending odor, or to dispense an insecticide, and so on. A common requirement is for air freshening in lavatories and bathrooms where special safety requirements and intermittent lighting may prevail. To add to safety and economy under these conditions various devices incorporating fans to move quantities of air across a fragrance dispenser have been suggested, as is evidenced by U.S. Pat. Nos. 4,857,240 and 4,568,521. U.S. Pat. No. 4,857,240 teaches the use of a battery powered fan to move air across a fragrance dispenser in response to a photoelectric cell. U.S. Pat. No. 4,568,521 teaches the use of a photovoltaic cell providing power to a motor connected to a fan to move air around a fragrance dispenser, the photovoltaic cell being mounted adjacent to a light bulb.

While these inventions add economy and safety for modifying ambient air in these environments, the instant invention offers important additional improvements. For example, in both of the above cited inventions a motor driven fan is required to move sufficient air across a fragrance dispenser in order to significantly effect the quality of the ambient air. And in the case of U.S. Pat. No. 4,568,521 the photovoltaic cell which powers the fan must be mounted adjacent a light bulb, the motor and fan combination necessarily going on and off in synchrony with said light bulb.

In the instant invention the aromatic substance to be dispensed is absorbed by a multi-paneled fragrance wheel mounted directly onto a motor shaft. The motor may be powered by conventional A.C. current, by battery, or most conveniently by photovoltaic cell. Ambient air is modified immediately as the wheel rotates on the motor, aromatic modifiers being dispensed in proportion to ambient lighting in the case of the photovoltaic cell powered motor rotation.

SUMMARY OF THE INVENTION

A primary object of the invention is to provide an economical fragrance dispenser.

An additional object is to provide an electrically safe fragrance dispenser for use in lavatories and bathrooms.

Another object is to provide a fragrance dispenser powered by ambient lighting.

A further object is to provide a modulated air fragrance dispenser for ambient air modification under low level lighting.

These and other objects are obtained with this motor driven fragrance wheel.

In the instant invention I find that by shaping the fragrance dispenser into the form of a multi-paneled wheel, and then connecting this wheel to the shaft of a motor, an efficient and economical fragrance dispenser results. For example, multiple layers of 100 point porosity absorbent cotton are stitched or cemented together, then they are die cut into the form of a 1"×1¼" rectangle with a concave configuration cut into the four sides of the rectangle. A hole is cut into the center of the rectangle, and this cotton fragrance "wheel" is not impregnated with approximately 4.5 grams of a suitable fragrance material. This cotton fragrance wheel is then placed in a polyethylene holder which has a hollow center post. This holder in turn nests in a nylon fragrance wheel retainer which similarly has a hollow center post for connection to the polyethylene holder and to the shaft of a motor. The purpose of the polyethylene holder is to form a convenient "package" for connecting and removing fragrance wheels as required. A variety of materials other than cotton may be employed as the fragrance material absorber, and other suitable materials for the holder and retainer may be employed, such as other plastics, metals, etc.

I find a high impact molded styrene case convenient and attractive for holding both the fragrance wheel and the motor for rotating the wheel. A shelf within the case provides a convenient platform for holding the fragrance wheel in the upper interior portion of the case, with the motor positioned and mounted to the underside of the shelf within the lower portion of the case. In the preferred embodiment wherein a photovoltaic cell is employed to power the motor, the motor is a low voltage D.C. motor which is electrically connected to a photovoltaic cell placed at the top of the case. This photovoltaic cell is protected by a suitable clear protective face plate, such as an acrylic face plate, or light transmission to the photovoltaic cell can be further enhanced by having this face plate be a "bubble" lens, as, for example, an acrylic bubble lens.

The styrene case can be substantially molded in one piece with a base, three walls, and internal shelf, and grooves for later attachment of a front panel. The internal shelf is for securing the motor within the bottom portion of the case, and a fragrance wheel within the upper portion of the case. The shelf has an approximate 5 degree pitch measured from the back wall of the case to the approximate area of the removable front wall of the case. This 5 degree pitch aids in the convenient insertion and removal of fragrance wheels as required.

The rotating shaft of the motor extends above the upper surface of the shelf within the case, and is easily rotatable. With the cotton fragrance wheel secured in its polyethylene holder, and the holder in turn secured in the nylon fragrance wheel retainer, the front panel on the case is removed, and the nylon fragrance wheel retainer is press fitted onto the motor shaft. The front panel is now put back into place.

Slits or louvers in three sides of the case provide for air circulation within the case and for propelling scented air from the case. If the case is now exposed to a source of light, current developed by the photovoltaic cell connected to the top of the case now causes the motor shaft to rotate. In this preferred embodiment utilizing a photovoltaic cell the motor is a low current, low voltage D.C. motor containing large numbers of very fine wire windings, and will therefore rotate even with very low current. Further, the motor being mounted in a substantially vertical position additionally reduces the load on the motor compared to the motor operating in a horizontal position. The fragrance wheel rotates rapidly, and therefore dispenses larger quantities of fragrance under bright lighting conditions, and will continue to rotate at lower lighting conditions, fragrance output being largely modulated by the amount of ambient light. In the absence of light, or insufficient lighting, the fragrance wheel remains quiescent.

Porous plastic materials can also make excellent fragrance wheels for use in this instant invention. For example, TESLIN (a registered trademark of PPG Industries, Inc.) is a single layer, highly filed microporous plastic film. It is a member of the polyolefin family of plastics, and contains approximately 65% of its volume as air. TESLIN film can be folded into an accordion style, multi-paneled fragrance wheel. This can be fabricated to fit into the same polyethylene holder and nylon fragrance wheel retainer previously described for the cotton fragrance wheel. The TESLIN fragrance wheel can be impregnated with a suitable fragrance liquid. In the case of this TESLIN fragrance wheel it has been found that a 100 point circular absorbent cotton pad placed between the TESLIN wheel and the polyethylene holder enhances the fragrance dispensing characteristics of the TESLIN wheel by acting as a reservoir for the fragrance.

Another example of a porous plastic suitable for making a fragrance wheel for this invention are porous granules of polyethylene. Granules having a specific porosity are pressed and formed by sintering into the desired shape. A pleated, multi-paneled wheel is molded out of polyethylene granules to form a polyethylene fragrance wheel. In this case a non-absorbing flat plate forms the base of the polyethylene fragrance wheel. Again a suitable fragrance liquid is impregnated into the porous polyethylene granules. The polyethylene fragrance w heel can be press fitted directly onto the motor shaft without the requirement for either a polyethylene holder or a nylon fragrance wheel retainer.

It should be noted that the TESLIN fragrance wheel and its polyethylene holder, and the polyethylene fragrance wheel can be recycled.

Thus it can be seen that an economical and efficient fragrance dispenser results from directly connecting a fragrance wheel to the rotating shaft of an electric motor. Fragrance is dispensed immediately as the motor shaft rotates without the necessity for a costly and cumbersome fan assembly to move ambient air across a fragrance dispensing pad. By making the motor a low current, low voltage D.C. motor powered by a photovoltaic cell the economy of operation in lavatories and bathrooms is assured. Additionally fragrance wheel rotation and therefore fragrance output to the ambient air peaks at desirable periods of maximum illumination insuring efficient room air modulation at those time periods when it is most required, with continued maintenance room air modulation during periods of lower illumination.

BRIEF DESCRIPTION OF THE DRAWINGS

FIG. 5 is a perspective view of one possible TESLIN fragrance wheel of the invention.

FIG. 6 is a perspective view of one possible polyethylene fragrance wheel of the invention.

FIG. 7 is a side schematic elevational view of the invention, illustrating a protective acrylic shield in place at the top of the case.

DETAILED DESCRIPTION OF THE PREFERRED EMBODIMENTS

Figure 1:
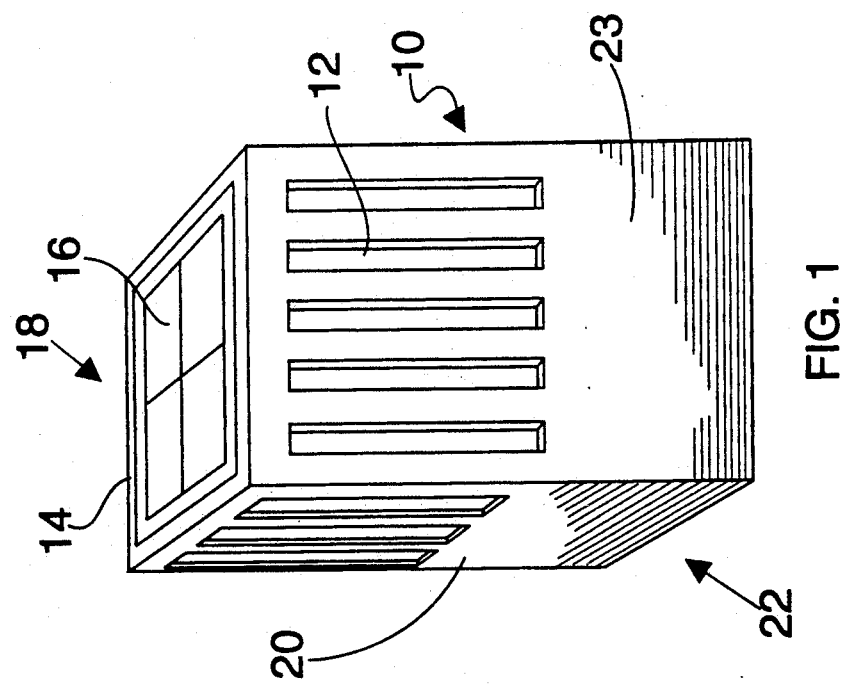
FIG. 1 is a perspective view of the case for the fragrance wheel and motor of the invention, illustrating a photovolaic cell in place at the top of the case.

Referring now to FIG. 1 a preferred embodiment of the case 10 of the invention is shown. A desirable method of fabrication is to mold case 10 out of high impact styrene. Typical measurements for the case are 2" wide $\times 2\frac{1}{4}$" long $\times 2\frac{3}{4}$" high. Slots 12 or louvers (not shown) are placed in side wall 23, rear wall 20, and the side wall opposite 23 (not shown) to provide adequate access of ambient air to the interior portion of case 10, and to provide adequate means for scented air within the case to be vented to the environment requiring air modulation. A photovoltaic cell 16 is shown in place at the top of case 10. The photovoltaic cell can be cemented at the top portion 18 of case 10 or otherwise permanently affixed to this top area. A clear cover 14 is cemented or otherwise affixed to case 10 above photovoltaic cell 16 with a spaced distance between cover 14 and photovoltaic cell 16. This protective cover 14 can be glass or clear plastic, such as an acrylic cover. A plate 22 forms the base of the case, with the front of the case 54 (FIG. 3) being removable from grooves (not shown) at the sides of the front of the case. A shelf 50 (FIG. 3) divides the interior of the case into approximately equal top and bottom portions. Shelf 50 can be molded in place within case 10 at an approximate 5 degree pitch 52 (FIG. 3) running from rear panel 22 to the front of the case.

Figure 2:
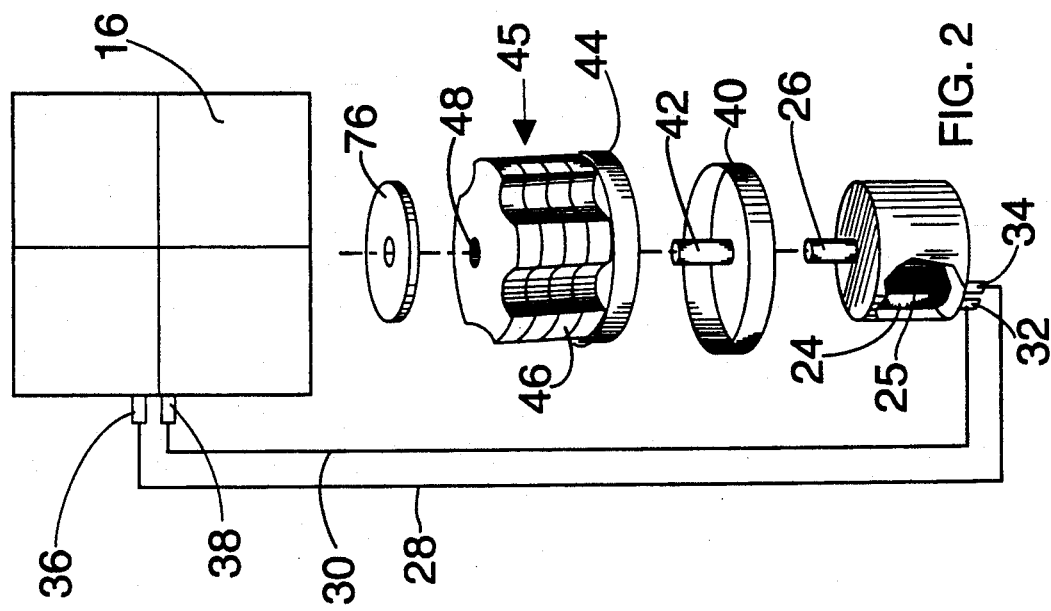
FIG. 2 is a schematic view of the operational components of the invention, with the fine wire windings for the motor shown in phantom.

FIG. 2 illustrates a preferred spatial arrangement of the functional components of the invention within case 10. A low current, low voltage D.C. motor 24 is connected by 22 gauge wires 28 and 30 to photovoltaic cell 16. Conductor 32 on motor 24 is connected by wire 30 to conductor 38 on photovoltaic cell 16, and conductor 34 on motor 24 is connected by wire 28 to conductor 36 on photovoltaic cell 16. Wires 28 and 30 pass through openings (not shown) in shelf 50 (FIG. 3) in order to make these connections. Motor 24 is part number SU-020 RA-12110, Mabuchi Type Motor, supplied by Mabuchi Motor America Corporation, 475 Park Avenue, New York, N.Y. 10016. Photovoltaic cell 16 is part number NSL-805 Silonex Type Cell, supplied by Silonex, Inc., 331 Cornella Street, Plattsburgh, N.Y. 12901. Motor 24 is further characterized by a large number of very fine wire windings 25 (FIG. 2) so that a low current will cause motor shaft 26 to rotate.

Figure 4:
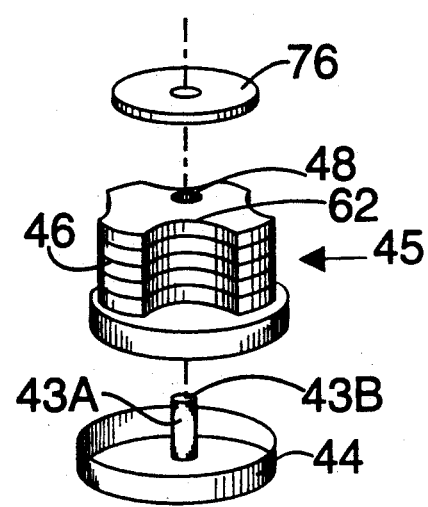
FIG. 4 is a perspective view of one possible cotton fragrance wheel of the invention.

FIG. 4 illustrates one preferred method of fabrication for the fragrance dispensing wheel of the invention. Layers 46 (e.g. 6 layers) of 100 point porosity absorbent cotton are die cut, and then cemented or stitched together. The die cutting yields a center hole 48 in cotton fragrance wheel 45 for subsequent connection to motor shaft 26. The die cutting also yields at least two concave cut outs 62 running the length of the cotton fragrance wheel to act as panels for moving air into and out of case 10 when cotton fragrance wheel 45 is rotated. Concave cut out 62 also acts as an extended surface area for fragrance dispensing. Typical dimensions of the cotton fragrance wheel are 1174" wide × ¾" high. Impregnating cotton fragrance wheel 45 with approximately 4.5 grams of a suitable aromatic liquid readies said cotton fragrance wheel for approximately 30 days of useful air modulation, whereupon said cotton fragrance wheel can be replaced or re-impregnated with said suitable aromatic liquid. Aromatic fragrances, insecticides and the like are conventional, well known to the art, and therefore will not be further discussed. Impregnated cotton fragrance wheel 45 is now placed in polyethylene holder 44, with hollow shaft 43A on polyethylene holder 44 extending upward into hole 48 at the center of the cotton fragrance wheel.

As can be seen in FIG. 2 the complete preferred assembly consists of a nylon fragrance wheel retainer 40 with its hollow shaft 42 being press fitted onto motor shaft 26, and polyethylene holder 44 being placed within nylon fragrance wheel retainer 40 with shaft 42 sliding into hollow shaft 43A via opening 43B in polyethylene holder 44. Finally nylon washer 76 is press fitted on top of polyethylene holder shaft 43A to secure the cotton fragrance wheel. Case 10 can now be fully closed by sliding front panel 54 in place.

Figure 3:
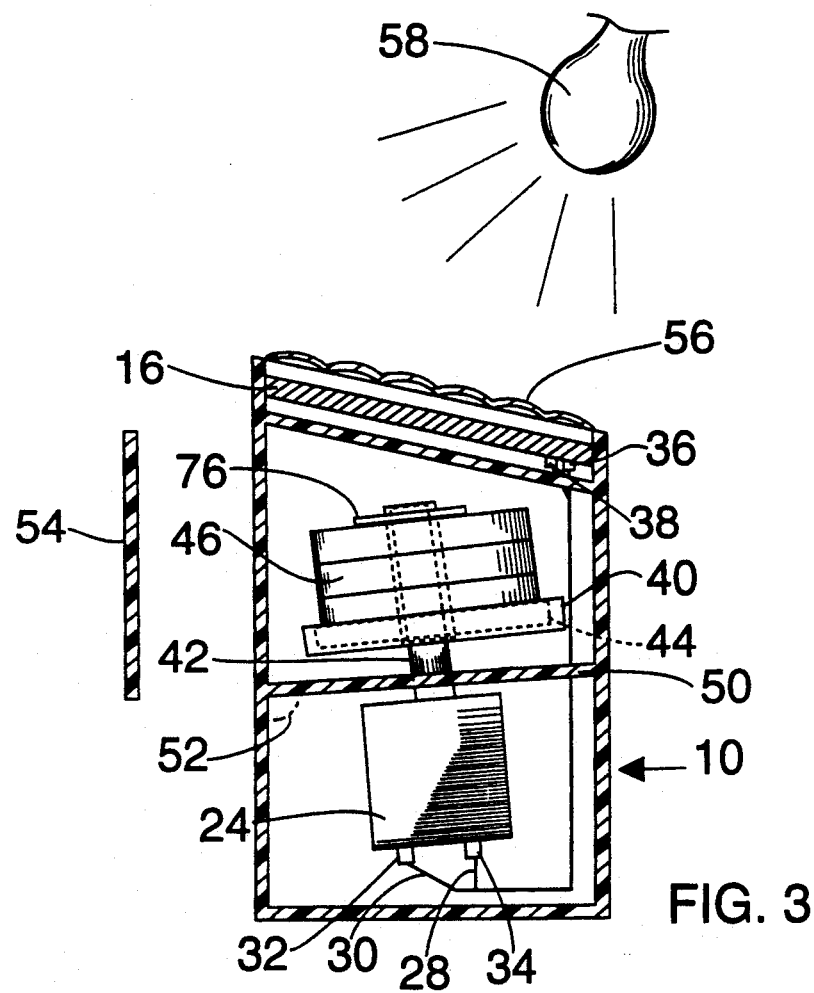
FIG. 3 is a side schematic elevational view of the invention, illustrating a bubble lens in place at the top of the case, with the front panel of the case in open position.

FIG. 3 illustrates the preferred arrangement of the components of the invention within case 10. Motor 24 is cemented to or otherwise affixed to the underside of shelf 50. Motor shaft 42 extends into the upper section of the interior of case 10 through a hole (not shown) in shelf 50. Nylon fragrance wheel retainer 40 snap fits over motor shaft 26 so as to provide a friction fit with said motor shaft. Cotton fragrance wheel 45, together with its nylon washer 76 and polyethylene holder, is assembled as described above, and is secured to nylon fragrance wheel retainer 40.

with electrical wiring in place as described between motor 24 and photovoltaic cell 16, turning on a source of illumination such as light bulb 58 will cause motor 24 to be energized, shaft 24 to rotate, which in turn rotates cotton fragrance wheel 45. Photovoltaic cell 16 provides about 1.0 to 2.5 volts D.C. and 100 ma. current to motor 24 in this embodiment. The photovoltaic cell will produce a current with either natural or artificial light, the quantity of current being proportional to the quantity of light falling upon cell 16. Under bright lighting conditions maximum current and therefore maximum fragrance dispensing is obtained, with lesser quantities of fragrance being dispensed under lower lighting conditions. To increase incident light transmission to photovoltaic cell 16, a bubble lens 56 (FIG. 3) such as, for example, an acrylic bubble lens, may be set in place above cell 16. After a period of time when the fragrance liquid is exhausted from said fragrance wheel, front panel 54 is simply removed to gain access to said fragrance wheel on said conveniently sloped shelf for replacement or replenishment.

FIG. 5 illustrates a second preferred embodiment of the fragrance wheel of the invention. Porous, liquid absorbing plastic materials, such as TESLIN, may be used to fabricate the fragrance dispensing wheel of the invention. TESLIN is a registered trademark of PPG Industries, Inc. TESLIN is a polyolefin plastic material. It is a single layer, highly filled, microporous plastic film. Approximately 65% of the volume of a TESLIN film is air. TESLIN film, approximately 0.018 inches in thickness, is folded into an accordion shaped TESLIN fragrance wheel 64, with multiple fan shaped panels 66 extending laterally from the central axis of said wheel 65. The TESLIN fragrance wheel is fabricated to fit into polyethylene holder 44 and nylon fragrance wheel retainer 40 as previously described for cotton fragrance wheel 45.. TESLIN fragrance wheel 64 measures approximately ¾" in length × 1¼" wide, and has a center hole 68 for connection to shaft 74 in polyethylene holder 44. A 100 point absorbent cotton reservoir ring 70 is placed over polyethylene holder shaft 74 between the TESLIN fragrance wheel and polyethylene holder 44 to act as a fragrance reservoir for enhancing fragrance dispensing from TESLIN fragrance wheel 64 which is now impregnated with approximately 4.5 grams of a suitable fragrance material. TESLIN fragrance wheel 64 is now assembled with polyethylene holder 44, and nylon fragrance wheel retainer 40, and motor 24 for fragrance dispensing to the ambient air.

A second preferred embodiment for a porous plastic fragrance wheel is illustrated in FIGS. 6 and 7. In this case granules of polyethylene with a specific porosity are pressed and sintered into the required shape. Porous polyethylene granules are available from Porex Technologies, 500 Bohannon Road, Fairburn, Ga. 30213-2828. For this application porous polyethylene granules with an average pore volume of 40% are selected. Pore volume for these granules should not exceed 65%. the polyethylene fragrance wheel is molded to a multi-paneled size and shape similar to that described for the TESLIN fragrance wheel 64. Polyethylene fragrance wheel 75 has a flat, base portion 78 coated with a non liquid absorbing material which eliminates the need for a holder for this fragrance wheel. Again, approximately 4.5 grams of a fragrance material is impregnated into polyethylene fragrance wheel 75, which in this case can be snap fitted directly to shaft 26 on motor 24 (FIG. 7) by means of center hole 80, whereupon fragrance is dispensed to the ambient air upon energizing of motor 24.

While the present invention has been disclosed in connection with the preferred embodiments shown and described in detail, various modifications and improvements will become readily apparent to those skilled in the art. Accordingly, the spirit and scope of the present invention is to be limited only by the following claims.

What is claimed is:

1. A fragrance dispenser comprising:
   (A) a fragrance dispensing wheel including at least two liquid absorbing panels extending laterally outwards from the central axis of said wheel;
   (B) a photovoltaic cell;
   (C) a motor having a rotatable shaft, said motor being electrically connected to, and energized by said photovoltaic cell;
   (D) a case for housing said fragrance wheel, said motor and said photovoltaic cell; and
   (E) means for connecting said wheel to said rotatable shaft on said motor so that when a fragrance material is added to said liquid absorbing panels and said motor is energized, said wheel rotates together with said shaft, and said fragrance material is dispensed to the ambient air contacted and moved by said wheel, wherein said case has a base, a top, and four walls, said walls containing openings for the movement of ambient air into and out of said case, said case further comprising means for mounting said motor and said fragrance wheel within said case, said motor being electrically connected to said photovoltaic cell, said photovoltaic cell being positioned at the top of said case, and substantially forming the top portion of said case so that ambient room lighting falling upon said top of said case is absorbed by said photovoltaic cell, and said cell then generates an electric current causing said shaft in said motor to rotate, which in turn rotates said wheel and said material so that said fragrance material is dispensed to said ambient air.

2. A fragrance dispenser according to claim 1 wherein said wheel has a hole at the center of said wheel for direct connection of said wheel to said rotatable shaft on said motor.

3. A fragrance dispenser according to claim 1 wherein said liquid absorbing panels are fabricated in absorbent cotton.

4. A fragrance dispenser according to claim 1 wherein said motor and said fragrance wheel are in vertical alignment with each other, with the fragrance wheel being positioned above said motor.

5. A fragrance dispenser according to claim 1 wherein said motor is capable of rotation at low voltage.

6. A fragrance dispenser according to claim 1 wherein said liquid absorbing panels are fabricated in porous, liquid absorbing plastic.

7. A fragrance dispenser according to claim 6 wherein said plastic is TESLIN.

8. A fragrance dispenser according to claim 6 wherein said plastic is polyethylene.

9. A fragrance dispenser according to claim 1 further comprising a clear covering for the outer light absorbing surface of said photovoltaic cell.

10. A fragrance dispenser according to claim 9 wherein said covering for said photovoltaic cell is a bubble lens.

* * * * *